United States Patent
Kim et al.

[11] Patent Number: 5,122,237
[45] Date of Patent: Jun. 16, 1992

[54] HIGH MOLECULAR HUMIDITY SENSOR AND MANUFACTURING METHOD THEREOF BY ELECTROCHEMICAL METHOD

[75] Inventors: Chung Y. Kim; Hee-Woo Rhee; Inseok Hwang; Jai K. Kim, all of Seoul, Rep. of Korea

[73] Assignee: Korea Institute of Science and Technology, Seoul, Rep. of Korea

[21] Appl. No.: 644,304

[22] Filed: Jan. 22, 1991

[30] Foreign Application Priority Data

Jul. 27, 1990 [KR] Rep. of Korea .......... 11492/1990

[51] Int. Cl.$^5$ .............................. C25D 9/02
[52] U.S. Cl. ................... 205/107; 204/430; 338/35; 73/335.02; 205/135; 205/159; 205/162; 205/221; 205/317
[58] Field of Search ......... 204/38.1, 430; 338/35; 73/336.5

[56] References Cited

U.S. PATENT DOCUMENTS

| | | | |
|---|---|---|---|
| 4,562,725 | 1/1986 | Oka et al. | 204/430 |
| 4,563,263 | 1/1986 | Oyama et al. | 204/433 |
| 4,707,244 | 11/1987 | Harman, III et al. | 204/430 |
| 4,791,374 | 12/1988 | Yodice et al. | 204/433 |
| 4,798,664 | 1/1989 | Yamaguchi et al. | 204/418 |
| 4,867,860 | 9/1989 | Siddiqui et al. | 204/418 |

FOREIGN PATENT DOCUMENTS

| | | |
|---|---|---|
| 24234 | 2/1984 | Japan . |
| 201244 | 10/1985 | Japan . |
| 133050 | 6/1988 | Japan . |
| 295153 | 11/1989 | Japan . |

*Primary Examiner*—John Niebling
*Assistant Examiner*—Kishor Mayekar
*Attorney, Agent, or Firm*—Fliesler, Dubb, Meyer & Lovejoy

[57] ABSTRACT

A high molecular humidity sensor and manufacturing method thereof in which polypyrrole being of conductive high molecule is electrochemically polymerized and then reduced whereby ionic conductive property is given so that humidity sensibility becomes excellent.

The high molecular humidity sensor of the invention is characterized in that it is a structure in which polypyrrole doped with dodecylsulfate anion $DS^-$ is stuck in film form on the surface of fine electrode, and cations $Na^+$, $K^+$ are permeated to said polypyrrole whereby salt is formed, and humidity sensibility is exhibited in region of $10^4$–$10^6$ $\Omega$, and humidity sensing speed becomes within several tens seconds to several minutes.

5 Claims, 2 Drawing Sheets

HIGH MOLECULAR HUMIDITY SENSOR AND MANUFACTURING METHOD THEREOF BY ELECTROCHEMICAL METHOD

BACKGROUND OF THE INVENTION

The present invention relates to a high molecular sensor and manufacturing method thereof in which polypyrrole which is a conductive high molecule is electrochemically polymerized and then reduced and thereby ionic conductivity is given so that humidity sensibility is made to be excellent.

High molecule having conjugated structure exhibits an electric conductivity essentially by doping, to which polyacetylene, polyparaphenylene, polyaniline, polyacene, polypyrrole, polythiophene, and polyfuran are included. These conductive high molecules are used for pH sensor, pressure sensor, sulphuric acid concentration sensor, oxygen and bionic sensor, and glucose sensor and the like. And, there are example used for alcohol and gas sensor as well as humidity sensor. Among which high molecules used for humidity sensor (Japanese laid-open patent publication No. 88-133050, 88-122758, 85-201244) were polyfuran, polythiophene, polyphyrrole, and heterocyclic compound of their derivatives, and wherein it was simple structure used with glass coated with indium tin oxide (ITO) for electrode of sensor, and separate reducing process for improving ionic conductivity was not executed. In such case, since there is limitation in humidity sensing speed and humidity measuring region, post-process for improving the precisely made sensor structure and ionic conductivity is required.

Polypyrrole, polythiophene, polyfuran and the like which are a kind of heterocyclic compound are electrochemically polymerized, at the same time a doping occurs to thereby exhibit electric conductivity. Therefore, the electric conductive mechanism may be said that electronic conduction and ionic conduction are operated in complex, and since the ionic conductivity produced at non-crystalloid within high molecule is weaker than electronic conductivity, it can be said that it is a conductivity by almost electronic conductivity.

SUMMARY OF THE INVENTION

Therefore, an object of the present invention is to provide a high molecular humidity sensor which is excellent in humidity sensibility and humidity sensing speed, and a method capable of manufacturing said high molecular humidity sensor electrochemically.

According to the polypyrrole used in the present invention among the heterocyclic high molecule that electrochemically polymerization is possible, polymer was formed in film type in organic solvent such as aqueous solution and acetonitrile, and conductivity at that time was more than 100 S/cm. Polypyrrole is good in chemical, thermal and atmospheric stability, and electrochemical property and physical property are different in accordance with the kind of pyrrole derivatives, copolymer or anion dopant.

The high molecular humidity sensor according to the present invention is characterized in that polypyrrole doped with dodecylsulfate anion $DS^-$ is covered and stuck in film form on the fine electrode surface and cations $Na^+$, $K^+$ are permeated into the polypyrrole whereby salt is formed, and humidity sensibility appears in the region of $10^4$ to $10^6$ $\Omega$ and humidity sensing speed is within several tens seconds to several minutes.

And, manufacturing method of high molecular humidity sensor according to the present invention is characterized in that the polypyrrole which is a conductive high molecule is electrochemically polymerized and thereafter being reduced whereby ionic conductivity is given.

BRIEF DESCRIPTION OF THE DRAWINGS

FIG. 2A to FIG. 2C are diagrams illustrating electrode structure and manufacturing process of high molecular sensor, in which FIG. 2A is an enlarged diagram of a photomask used in photolithography, FIG. 2B is a diagram showing an electrode structure before polymerizing the polypyrrole, FIG. 2C is a diagram showing an electrode structure after polymerizing the polypyrrole.

DETAILED DESCRIPTION OF THE INVENTION

Hereinafter, the present invention will be described in detail with reference to the accompanying drawings.

Figure 1:
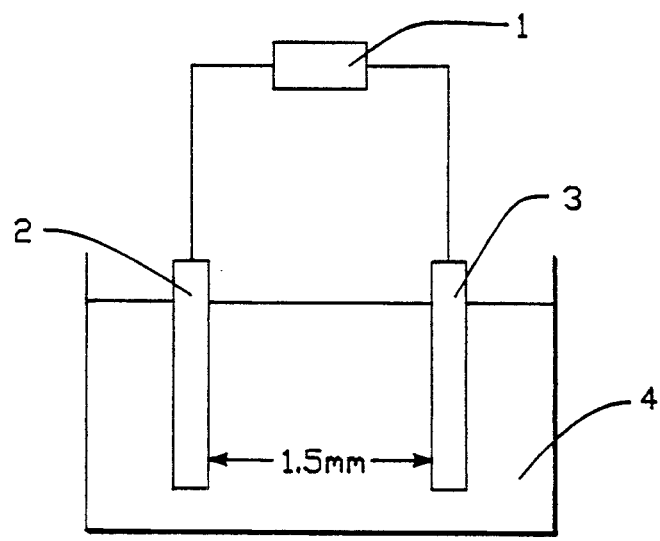
FIG. 1 is a schematic structural diagram of electric polymerizing reaction bath.

FIG. 1 is a schematic diagram of an electric polymerizing reaction bath, wherein reference numeral 1 is a direct current-voltage source, numeral 2 is an operating electrode, and numeral 3 is opposite electrode Pt. Fine electrode which is designed and manufactured by photolithographic method is placed for operating electrode. Reference numeral 4 is electrolyte, which is TBADS/ACN or NaDS/H$_2$O group included with pyrrole which is a monomer upon polymerizing, while it is aqueous solution group included with small cation such as $Na^+$ and $K^+$ upon reducing.

Figure 2A:
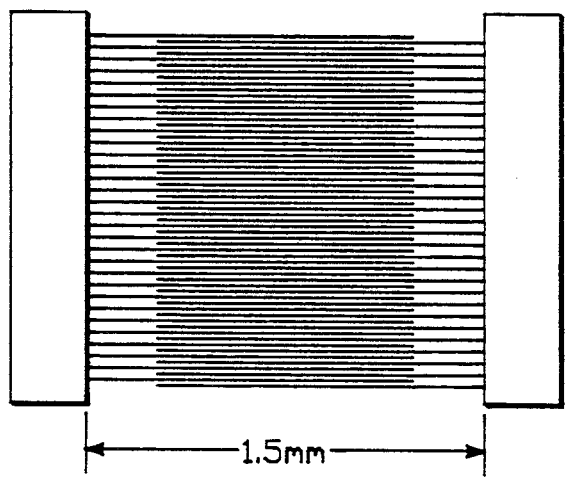
Figures 2B, 2C:
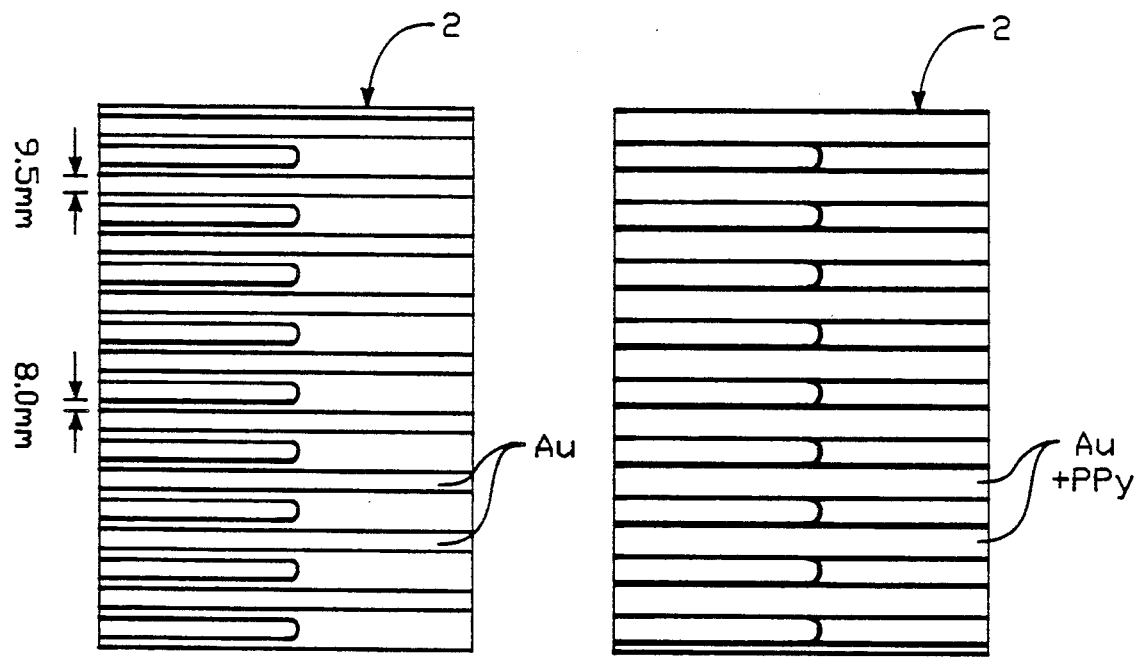

FIG. 2A to 2C are diagrams showing electrode structure of high molecular sensor, in which FIG. 2A is a magnified photograph of photomask structure used in photolithographic method, FIG. 2B is an enlarged photograph showing electrode arrangement before polymerization of polypyrrole, and FIG. 2C is an enlarged photograph of electrode arrangement after polymerization of polypyrrole, While the polymerization is proceeded, the polypyrrole of dark color of FIG. 2C was grown at brightly viewing gold electrode of FIG. 2B and around it.

Figure 3:
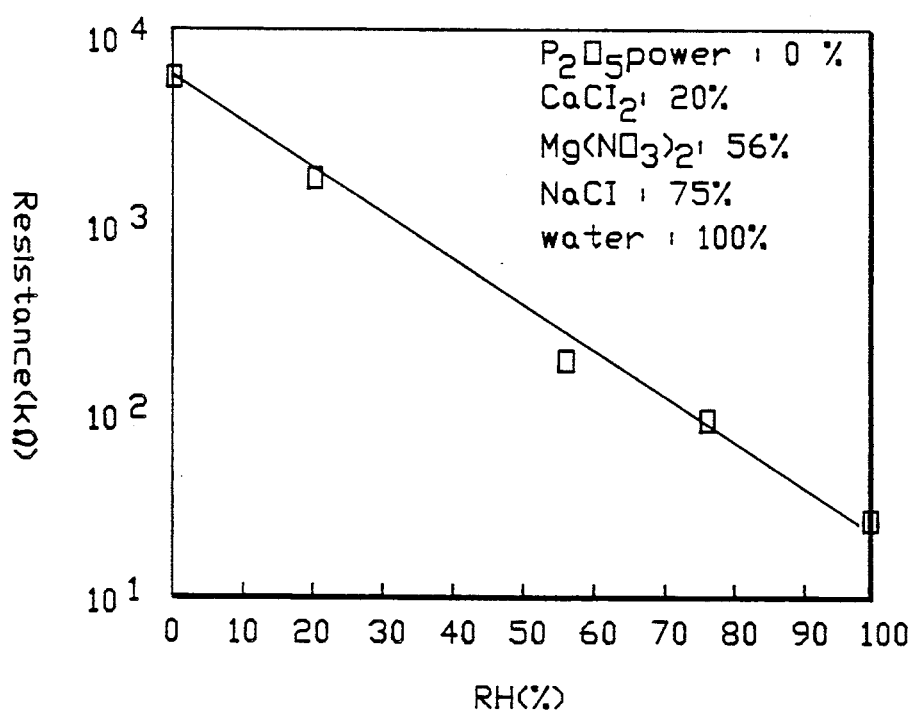
FIG. 3 is a graph of humidity sensibility of polypyrrole humidity sensor.

FIG. 3 is a graph of humidity sensibility of the polypyrrole sensor (25° C.) which is TBADS/ACN group for electrolyte used upon polymerizing, while it is KClO$_4$/water group upon reducing.

In manufacturing the high molecular humidity sensor according to the present invention, anhydrous calcium chloride CaCl$_2$ was added to monomer pyrrole (Aldrich 90%) to be used and being dried primarily and then calcium hydride CaH$_2$ was added again and distilled under reduced pressure and refined and thereafter said refined pyrrole was polymerized. When the pyrrole was polymerized, polymerizing reaction was taken place and simultaneously radical intermediate was formed, and since the radical intermediate was influenced according to the nucleophilic degree of the electrolyte and solvent, attention was taken for the selection of it. In the present invention, tetrabutylammonium dodecylsulfate TBADS (Korean Patent Application No. 18889, filed Dec. 19, 1989) synthesized by inventors of this application was used for the electrolyte to sodium dodecylsulfate NaDS or acetonitrile which is a nonprotonic solvent. When the pyrrole is electrochemically polymerized in the reaction bath of FIG. 1 by using electrolyte of NaDS or TBADS group, dodecylsulfate ion $DS^-$ is doped whereby electric conductivity is exhibited. On the other hand, even if this pyrrole is reduced for long time (24 hours) by a voltage ($-2.5V$) of reverse polarity against polymerizing time in aqueous solution group such as NaDS/water, large $DS^-$ can not get out of film, instead, relatively smaller cation gets into the film and becoming gradually to electrical neutrality. This was confirmed by EDS/EPMA (Energy dispersive X-ray spectrometer/electronprobe microanalyzor). If the film is not extremely thin, complete electric neutrality is difficult to obtain, and at this moment, conduction mechanism of polypyrrole is caused by electronic conduction as well as ionic conduction.

Fine electrode of high molecular humidity sensor used in the present invention was manufactured on the glass or alumina base plate by photolithographic method.

Tungsten was made to surface film on the base plate by sputtering method, and nickel was deposited thereon by thermal evaporation Selection of the base plate and coating of tungsten and nickel and the like have relation with durability of sensor electrode. Positive photoresist was coated thereon again and then infrared ray was permeated through photomask designed as FIG. 2A in electrode structure whereby image was formed. And then, gold plating was executed to the portion etched as designed structure and thereafter positive photoresist, nickel, and tungsten were etched in turn whereby fine electrode was manufactured. The structure of fine electrode was a form that two comb teeth pattern electrodes are alternately arranged one another, and interval between them was 7.8-9.5μm. The electrode structure was designed so as to have minute interval and arrangement as far as possible, and this is for making the resistance of high molecular sensor to reduce toward measuring region and making the electrostatic capacity to be larger so that humidity sensibility is maximized. The fine electrode was placed for positive (+) electrode of electric polymerizing reaction bath of FIG. 1 and when leg of polypyrrole was formed between the intervals of the fine electrode then the polymerization was stopped. Thickness of polymerized polypyrrole was adjusted by controlling electric current quantity (1-5mA) or polymerizing time (5-15 seconds). And next, the eletrolytic solution was changed to aqueous solution including small cation and then reduced whereby cation was permeated. At this moment, the voltage ($-0.5$ to $-1.0V$) and reducing time (3-10 minutes) are controlled, so that reducing degree of the film, that is, ionic conductive property was given The humidity sensibility of thus manufactured high molecular sensor was appeared in the region of $10^4$-$10^6$ $\Omega$, and the humidity sensing speed was also good as within several tens seconds to several minutes.

Hereinafter, examples of aforementioned present invention will be described in detail as followings.

EXAMPLE 1

All experiments were carried out in the one-compartment electrolytic bath (40cc) of FIG. 1.

Fine electrode manufactured by photolithographic method was tightly placed for positive electrode (+) and platinum electrode (3×6cm) for negative electrode (−), and the distance between them was maintained by 1.5mm. The electrolyte TBADS was dissolved to 40cc of acetonitrile so as to become 0.036mol/l. The pyrrole was added with calcium chloride $CaCl_2$ and was dried primarily and was dried secondarily by calcium hydride $CaH_2$ as distilled in reduced pressure (22°-25° C.). Concentration of pyrrole used upon polymerizing was 0.036mol/l. The polymerization was executed for 10 seconds by flowing current of 3mA at 20°-25° C. In order to execute reduction, voltage of $-0.75V$ was applied for 5 minutes in the device of FIG. 1 with electrolyte for aqueous solution of potassium perchlorate $KClO_4$.

Thus, electronic conduction was lowered and ionic conduction property was relatively increased.

In FIGS. 2B and 2C, the distance between the electrodes was 7.8-9.5 μm. As can be seen from FIG. 2C, while the polymerization is proceeded, polypyrrole film is formd on each electrode, and when it reaches the thickness of a predetermined degree, leg of polypyrrole is formed at the interval between the electrodes FIG. 3 shows the resistance change of high molecular humidity sensor in response to the relative humidity RH % maintained with saturated aqueous solution of various salts, and the polypyrrole is a state that it is polymerized in TBADS/ACN and then reduced in $KClO_4$/water. Relative humidity 100% was maintained by distilled water, and relative humidity 0% by $P_2O_5$ powder.

EXAMPLE 2

All experimental conditions were same as example 1, and it was reduced by aqueous solution of $NaClO_4$ as electrolyte.

EXAMPLE 3

All experimental conditions were same as example 1, and aqueous solution of NaDS was used as electrolyte upon polymerizing.

EXAMPLE 4

All experimental conditions were same as example2, and aqueous solution of NaDS was used as electrolyte upon polymerizing.

The high molecular humidity sensor of the present invention has advantage that humidity sensibility and humidity sensing speed are excellent.

What is claimed is:

1. A manufacturing method of high molecular humidity sensor comprising:
   a polymerizing step in which electrolytic solution mixed with monomer pyrrole to a solution including dodecylsulfate anion $DS^-$ of large molecular weight is utilized, a fine electrode having sensor structure is placed for a positive electrode and a platinum plate is placed for a negative electrode while a direct current power is supplied, whereby polypyrrole doped with said anion $DS^-$ to said positive electrode is formed in film shape; and
   a reducing step in which electrolytic aqueous solution containing small sized cations $Na^+$, $K^+$ is utilized, and a direct current power of reverse polarities are respectively supplied to said positive electrode and negative electrode, whereby detaining said anion $DS^-$ to said polypyrrole and permeating said cations $Na^+$, $K^+$ to form a salt-and then giving an ionic conductivity.

2. The method as claimed in claim 1, wherein said polymerizing electrolytic solution is mixed with tetrabutylammonium dodecylsulfate TBADS as electrolyte to acetonitrile ACN which is nonprotonic solvent.

3. The method as claimed in claim 1, wherein said polymerizing electrolytic solution is aqueous solution of sodium dodecylsulfate NaDS.

4. The method as claimed in claim 1, wherein.
electrode to be applied with positive polarity upon said polymerization is fine electrode in which tungsten and nickel are stuck in film form in turn on a base plate of glass or alumina, and positive photoresist is coated and then image is formed by a structure designed by photolithography, and
gold plating is executed to etched portion and the positive photoresist, nickel, and tungsten are etched in turn to thereby be formed in comb teeth pattern in which partial electrodes of longer width portions and shorter width portions are alternately arranged.

5. The method as claimed in claim 1, wherein intervals between each partial electrodes of said fine electrode are 7.8–9.5 $\mu$m.

* * * * *